United States Patent
Giles (10) Patent No.: US 12,293,240 B2
(45) Date of Patent: May 6, 2025

(54) MULTI-TENANT NURSE CALL SYSTEM WITH SHARED WORKFLOWS

(71) Applicant: TigerConnect, Inc., Santa Monica, CA (US)

(72) Inventor: Stephen Giles, Jacksonville, FL (US)

(73) Assignee: TigerConnect, Inc., Santa Monica, CA (US)

( * ) Notice: Subject to any disclaimer, the term of this patent is extended or adjusted under 35 U.S.C. 154(b) by 265 days.

(21) Appl. No.: 17/499,373

(22) Filed: Oct. 12, 2021

(65) Prior Publication Data

US 2022/0066838 A1   Mar. 3, 2022

Related U.S. Application Data

(63) Continuation-in-part of application No. 16/122,379, filed on Sep. 5, 2018, now abandoned.

(51) Int. Cl.
| | |
|---|---|
| G06Q 10/00 | (2023.01) |
| G06F 9/00 | (2018.01) |
| G06F 9/50 | (2006.01) |
| G06Q 10/0631 | (2023.01) |
| G16H 40/00 | (2018.01) |
| G16H 40/60 | (2018.01) |
| G16H 80/00 | (2018.01) |

(52) U.S. Cl.
CPC .......... *G06F 9/5088* (2013.01); *G06F 9/5038* (2013.01); *G06Q 10/06311* (2013.01); *G16H 40/60* (2018.01); *G16H 80/00* (2018.01)

(58) Field of Classification Search
CPC ...................................................... G16H 40/20
See application file for complete search history.

(56) References Cited

U.S. PATENT DOCUMENTS

| | | | |
|---|---|---|---|
| 2012/0119890 A1* | 5/2012 | Collins, Jr. .......... | G08B 25/016 340/286.07 |
| 2015/0310176 A1* | 10/2015 | Chen ..................... | H04L 51/214 705/2 |
| 2018/0043096 A1* | 2/2018 | Dobbles ............ | A61M 15/0068 |

OTHER PUBLICATIONS

E. Elnahrawy and R. P. Martin, "Studying the utility of tracking systems in improving healthcare workflow," 2010 8th IEEE International Conference on Pervasive Computing and Communications Workshops (PERCOM Workshops), Mannheim, Germany, 2010, pp. 310-315, doi: 10.1109/PERCOMW.2010.5470651. (Year: 2010).*

* cited by examiner

*Primary Examiner* — Matheus Ribeiro Stivaletti
(74) *Attorney, Agent, or Firm* — White and Williams LLP (57) ABSTRACT

A multi-tenant nurse call system (MTNCS) has functionality that operates to receive event messages having information corresponding to an event type and device identity that it uses to select a workflow comprised of a set of ordered business rules that when run is designed to respond to the event. The MTNCS can be configured so that different workflows can be triggered by the same type of event message depending upon the identity of the tenant that generated the event message, and it can be configured so that a workflow can be paused or terminated during a period of time during which the MTNCS waits to receive subsequent similar events as the one that triggered the workflow.

17 Claims, 10 Drawing Sheets

EVENT-WORKFLOW LOOKUP 343

| EVENT TYPE ID | WORK FLOW ID |
|---|---|
| ET-01 | ----------► WF-01 |
| ET-02 | ----------► WF-02 |
| ET-03 | ----------► WF-03 |

FIG. 4B

WORKFLOW DEFINIION TABLE 344

| WF.ID | RULE SET | TENANT CONFIG. |
|---|---|---|
| WF-01 | RULES-01 | TENANT-A CONFIG/TENANT-B CONFIG |
| WF-02 | RULES-02 | TENANT-B CONFIG |
| WF-03 | RULES-03 | TENANT-C CONFIG |

FIG. 4C

DEVICE – TENANT TABLE 345

| DEV.ID | CURRENT TENANT CODE |
|---|---|
| DEV-01 | TC-A |
| DEV-02 | TC-B |
| DEV-03 | TC-B |

FIG. 4D

DEVICE DEFINITION TABLE 346

| DEV.ID | DEV.DEF.FILE | TENANT CONFIG. |
|---|---|---|
| DEV.01 | CONFIG. INFO | TENANT.A/TENANT.B |

FIG. 4E

```
EVENT-WORKFLOW LOOKUP 347

EVENT TYPE ID/T.C.            WORK FLOW ID

WORKFLOW.01

"Pillow Speaker Beep" workflow

- Triggered by: "Bed A Beep" or "Bed B Beep" button pushes (call types)
- Lights activated when active: Yellow
- Priority of secondary notification messages sent to staffers during the steps of this workflow: Low
- Allow Staffers to Accept or Reject when assigned to this workflow: Yes
- Remind accepting staffers: Once every 2 minutes, for 8 total minutes
- Remind everyone, if no more assignments: Once every 5 minutes for 30 total minutes
- 1st step after Workflow starts: Assign to all staff roles for active shift in this unit
- 2nd step: Wait for 1 minute
- 3rd step: Escalation (Assign again to all staff roles for unit's active shift)
- 4th step: Wait for 1 minute
- 5th step: Reminder message
- Workflow Stops On: Staff Presence detected (Level 0 – 3 accepted), OR Cancel Button pushed on Patient Station

FIG. 5B

WORKFLOW.01w/SUSPEND STEP

"Pillow Speaker Beep" workflow

- Triggered by: "Bed A Beep" or "Bed B Beep" button pushes (call types)
- Lights activated when active: Yellow
- Priority of secondary notification messages sent to staffers during the steps of this workflow: Low
- Allow Staffers to Accept or Reject when assigned to this workflow: Yes
- Remind accepting staffers: Once every 2 minutes, for 8 total minutes
- Remind everyone, if no more assignments: Once every 5 minutes for 30 total minutes
- 1st step after Workflow starts: Assign to all staff roles for active shift in this unit
- 2nd step: Suspend: Suspend period = 60 seconds, threshold number = 3
- 3rd Step: Wait for 1 minute
- 4th step: Escalation (Assign again to all staff roles for unit's active shift)
- 5th step: Wait for 1 minute
- 6th step: Reminder message
- Workflow Stops On: Staff Presence detected (Level 0 – 3 accepted), OR Cancel Button pushed on Patient Station

FIG. 5C

WORKFLOW.01 w/Auto-Stop

"Pillow Speaker Beep" workflow

- Auto-Stop Selection: <u>Active</u>/Inactive
- Triggered by: "Bed A Beep" or "Bed B Beep" button pushes (call types)
- Lights activated when active: Yellow
- Priority of secondary notification messages sent to staffers during the steps of this workflow: Low
- Allow Staffers to Accept or Reject when assigned to this workflow: Yes
- Remind accepting staffers: Once every 2 minutes, for 8 total minutes
- Remind everyone, if no more assignments: Once every 5 minutes for 30 total minutes
- $1^{st}$ step after Workflow starts: Assign to all staff roles for active shift in this unit
- $2^{nd}$ step: Wait for 1 minute
- $3^{rd}$ step: Escalation (Assign again to all staff roles for unit's active shift)
- $4^{th}$ step: Wait for 1 minute
- $5^{th}$ step: Reminder message
- Workflow Stops On: Staff Presence detected (Level 0 – 3 accepted), OR Cancel Button pushed on Patient Station

MULTI-TENANT NURSE CALL SYSTEM WITH SHARED WORKFLOWS

FIELD OF THE INVENTION

The present disclosure relates generally to the operation of multi-tenant database systems and specifically to a multi-tenant nurse call system that can share configuration information between tenants.

BACKGROUND

For different reasons, some organizations divide their business into smaller operational units that are in some manner related to the larger, parent organization. For example, many hospitals are organized into units that logically defined according to one or more specialized medical disciplines or logically defined according to a grouping of rooms. A unit can comprise one or more emergency, pediatric, critical care, in-patient, out-patient or surgical rooms in a hospital. Generally, the operation of each one of these specialized units is supported by hardware, software and communication systems that are dedicated to each unit and which need to be individually configured to support the operation of each unit. The hardware in this case can be different types of patient monitors, intelligent patient beds, and nurse call system hardware and software. With respect to hardware system configuration, similar patient monitors or beds in two hospital units can be configured similarly or differently to generate and send event information for processing to a nurse call system that is dedicated to that unit. For example, one monitor can be configured to generate and send event information to a nurse call system if a patient heart rate drops below seventy beats per minute, and another, similar monitor can be configured to generate an event if a patient heart rate drops below sixty beats per minute. Similarly, a first nurse call system operating in support of one hospital unit may be configured to process information it receives from the hardware or communication devices assigned to that unit differently than another second nurse call system operating in support of another hospital unit. In this regard, the first nurse call system could be configured to play an audible alarm in response to receiving event information and the second nurse call system could respond to the same type of event by illuminating a particular color of light on a console associate with the nurse call system.

DETAILED DESCRIPTION

Each nurse call system that is dedicated to a specialty unit can have a dedicated store of information that is, to some extent, a duplicate of information maintained by nurse call systems dedicated to supporting other units. In such an arrangement of nurse call systems, hardware device and application software configuration information can be duplicated, and the process for configuring and maintaining separate nurse call systems is both inefficient and time-consuming. Further, hospital staff, patients and medical devices can frequently move from one unit to another unit according to patient treatment and monitoring needs and according to staff schedules, all of which further hinders the efficient operation and maintenance of a nurse call system. Generally, database systems can be designed to maintain the information needed to support the operation of a nurse call system. Database systems are in use that operate to maintain information that can be shared among multiple users according to permissions granted to each user or tenant, and such a database system is referred to as a multi-tenant database system. In the context of a hospital setting, and in accordance with this description, a tenant can be any logical, self-contained grouping of one or more kinds of a clinical entity. The types of entities that can be classified as the same tenant can include, but is not limited to, one or more hospital specialty unit (i.e., ER, Cardiac Unit, etc.) hospital staff, patients, NurseCall signaling devices, messaging devices, facilities, web administration app users, and workflow definitions. All entities within the same tenant can be permitted access to database information related to that tenant. If an entity (such as a web user) has been associated with an additional tenant, then it is also able to access information related to that other tenant as well. The entities under a given tenant may be located in a contiguous area or not, they can be located in the same facility or they can be distributed across multiple facilities that are in different geographic locations.

In lieu of the disadvantages associated with duplicating information to be used by multiple, different tenants, it would be advantageous if information associated with the provision of services is shared with one or more other tenants so that the same information does not have to be replicated between tenants. Accordingly, we have designed a multi-tenant nurse call system (MTNCS) that maintains information in a multi-tenant database system that can be configured to be shared or partitioned between tenants according a scheme that is configured by a system administrator with knowledge of interactions between multiple tenants, or automatically and dynamically according to staff schedules and current staff (i.e. teams or individuals) or device locations. Information comprising the MTNCS can include patient medical records, the location of each patient or medical device, staff schedules and assignments, and it can include hardware device configuration information, software application configuration information and configurable workflow information used by MTNCS to process event information received from patient monitors or nurses or a team of medical professionals associated with a particular tenant.

According to one embodiment, the MTNCS can be configured to process event information generated by a first tenant using a particular workflow assigned only to that tenant (i.e., a partitioned workflow), or which can be shared with two or more other tenants (a shared workflow), and each workflow is comprised of a set of ordered business rules. Any one of the workflows can be either statically or dynamically shared between two or more tenants. If configured to be shared dynamically, a workflow configured to operate in association with the first tenant can be shared with other tenants based upon movement of an individual or team (i.e., staff or patient), or movement of a medical device from the first tenant location to another second tenant location, or the workflow sharing can be based upon a schedule that assigns a staff member or members to perform duties at different times in any one of the plurality of the tenant locations.

According to another embodiment, the MTNCS can be configured to process event information received from one device that is shared between multiple tenants. Operating in this manner, patient beds and monitoring equipment can be shared between multiple tenants, and it is not necessary to re-configure the MTNCS to process event information from a shared hospital device.

According to another embodiment, the MTNCS can be configured to support the operation of multiple services, such as a messaging service, a nurse call service, a rules processing service, and a location tracking service. Each of these services can be run as single instances on one virtual machine, or can be scaled out to run on multiple virtual machines and statically or dynamically configured to run under separate tenant(s) in order to distribute the workload. In the event that a first tenant is currently busier in some manner than another second tenant (i.e., experiencing more emergencies or a higher nurse call volume), one or more idle VMs can be initialized and assigned to run services for the first tenant, while the second tenant can continue to be served by the same or fewer VMs. Dynamically configuring the MTNCS to operate in this manner permits the system to efficiently utilize a limited amount of processing resources. According to this description, two or more tenants can be located in the same physical space or not, and so the sharing of workflow instances between tenants is not necessarily dependent upon a current staff location, but a current staff or device assignment.

According to another embodiment, an event of the same type generated by devices associated with different tenants can result in the MTNCS starting a different workflow.

Further, and according to another embodiment, a workflow can be configured to be self-correcting such that after it is triggered to start by a particular event, the workflow can be configured to be temporarily suspended or paused until one or more similar events are detected before some selected, configurable period of time expires, in which case the workflow can proceed, or in the alternative terminate. Alternatively, a background process can be running that can automatically stop a workflow at any time if an event, similar to the one that triggered the workflow, is not detected before some selected, configurable period of time expires. In this regard, the workflow can stop immediately before a current step has completed, or stop after it completes a current workflow step.

Figure 1:
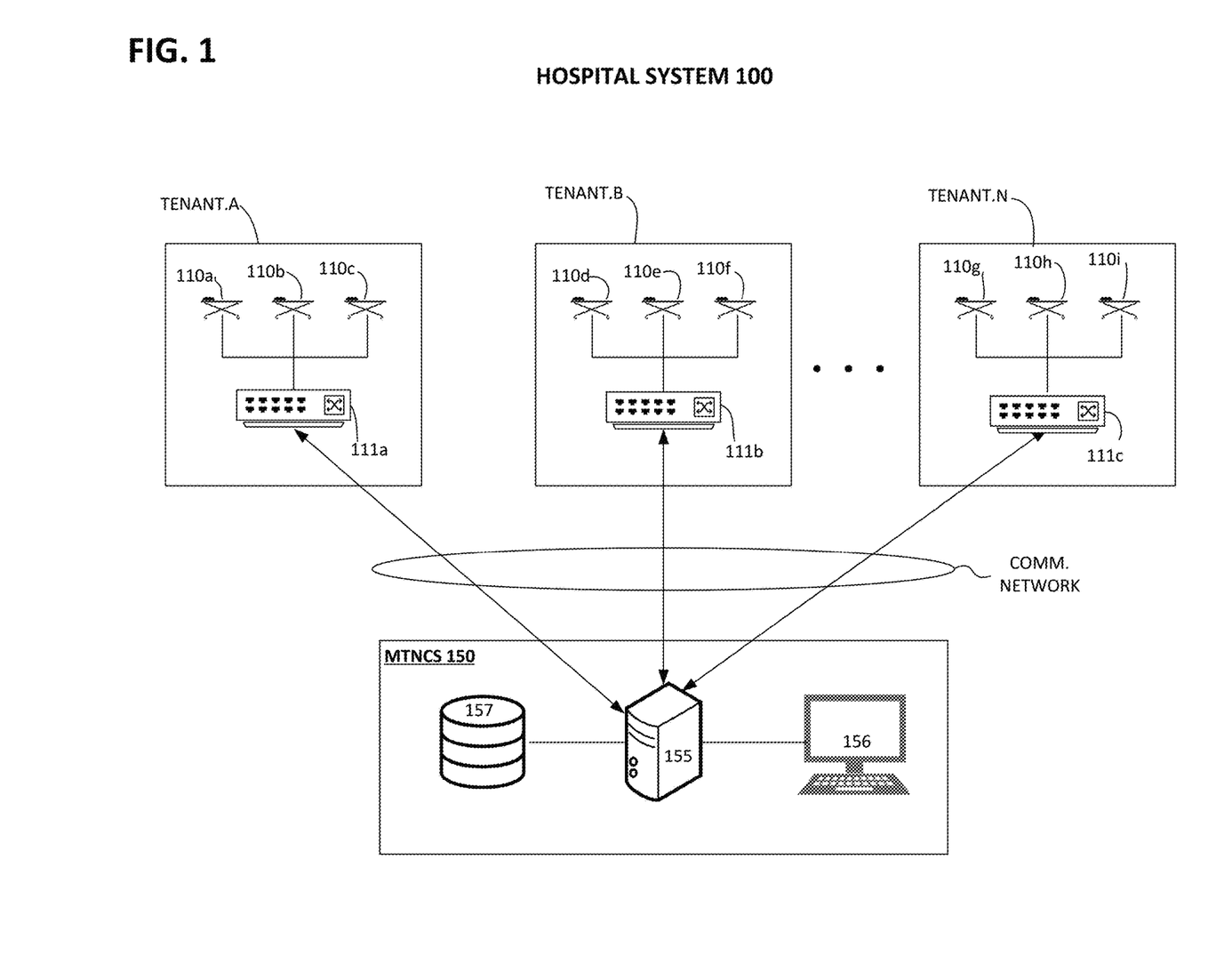
FIG. 1 is a diagram illustrating a hospital system 100.

An MTNCS 150, such as the one described above, is shown in FIG. 1 and labeled MTNCS 150. FIG. 1 illustrates a plurality of tenants, Tenant.A, Tenant.B to Tenant.N, with N being an integer number, and the MTNCS 150 that are able to communication with each other over a wired network, wireless network, or some combination of the two. The communication network can be a local network such as an Ethernet, or it can be a wide-area network such as the Internet, or it can be a combination of local and wide area networks. Each of the tenants has some number of patient beds labeled 110a-110i, patient monitoring devices (not shown) that operate to detect physiological information from a patient such as heart rate, blood pressure or other physiological information, and communication devices (also not shown) all of which are connected in a wired or wireless manner to a switch, router or some other communications processing device labeled 111a-111c and which operate to transmit event information received from the beds, monitors, communication devices comprising each tenant to a server 155 comprising the MTNCS 150 which operates to process event information (i.e., a heart rate or blood pressure is detected to be to slow or to low respectively) generated by a medical device associated with each tenant having access to the system 150. The NTNCS also has a database 157 that operates to maintain information that can be shared or partitioned among multiple tenants, and it has a console 156 that functions to display or play results of event message processing by the server 155.

Figure 2:
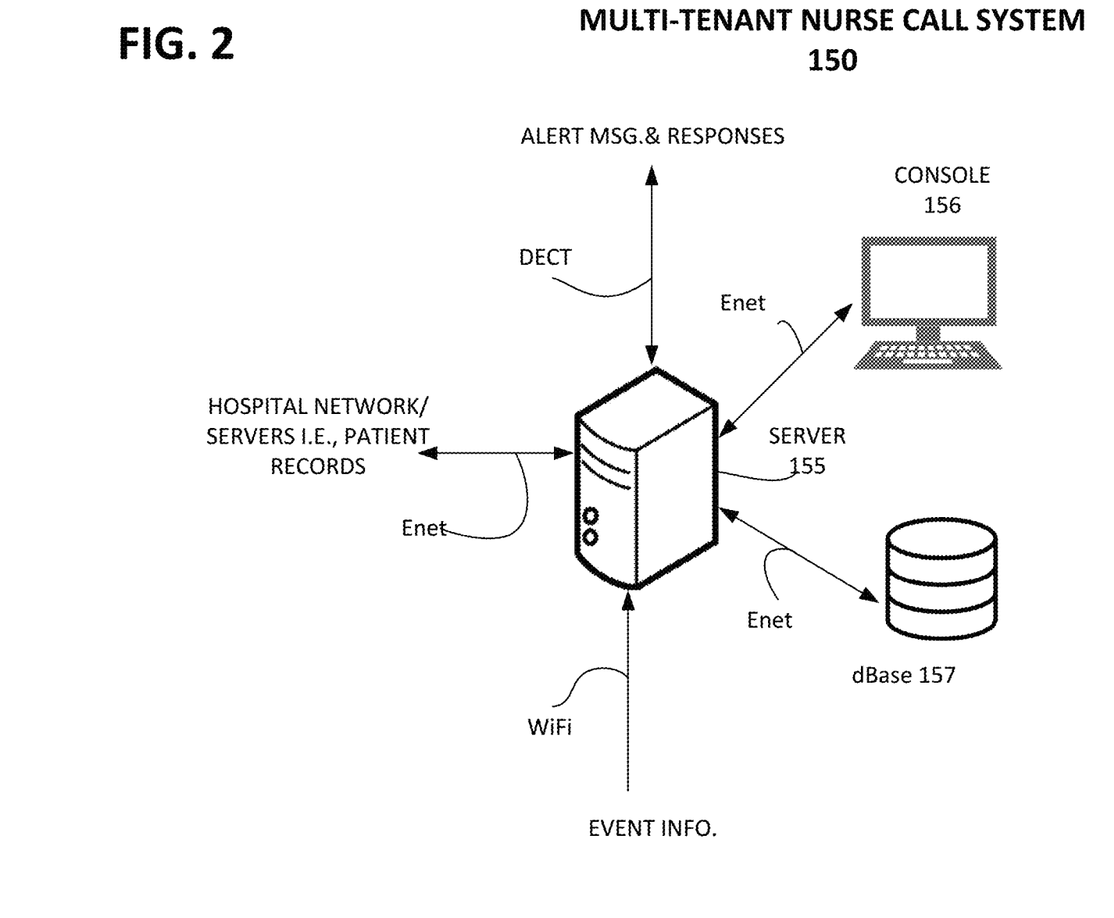
FIG. 2 is a diagram illustrating a multi-tenant nurse call system (MTNCS) 150.

FIG. 2 is a diagram illustrating the MTNCS 150 connectivity to various networks over which it receives and transmits information from any of the multiple tenants authorized to use the system. As shown in FIG. 2, the server 155 is connected to one or more hospital servers that maintain current patient medical record information such as age, DOB, physical characteristics, health insurance and other patient information. The server 155 can also be connected to a wireless network (Wi-Fi/DECT/BT) over which it can receive event information from patients, patient bed, patient monitors or information from staff that it processes and determines what action, if any, should be taken in response to the received information. Event information in this case can be information in a message generated and sent by a patient monitor that corresponds to a current physiological characteristic of a patient, such as heart rate, respiratory rate, etc. The server 155 is also connected to the database 157 which can maintain, among other things, current patient/device/staff locations, current patient medical status and pharmaceutical requirements, it can also maintain staffing information for each tenant such as individual responsibilities and schedules, and it can maintain information that can be utilized by the MTNCS 150 to initiate the performance of activities associated with the care of a patient and to maintain information associated with hospital hardware devices such as patient beds and patient monitors. At least some of the information that is maintained in the database 157 for use by the MTNCS 150 can be configured to be shared between multiple tenants, or the information can be partitioned to only be accessible by a single tenant. Consequently, and depending upon how the information maintained in the database 157 is configured, the server 155 can respond to an event generated by an individual staff member that is currently associated with any one of two or more different tenants by selecting an appropriate course of action that is configured to be shared between any of the different tenants, and then the server can initiate a series of steps to ensure that the selected course of action has been completed. Accordingly, the MTNCS 150 is able to process event information generated by hospital staff as they move seamlessly from one tenant to another tenant.

Considered together, the series of steps comprising the course of action described above is referred to here as a workflow, and each different workflow is comprised of an ordered series of two or more steps, or business rules, that determine how the course of action is performed. Finally, the server 155 can be connected to a console 156 that operates to display or play information relating to events or to the status of a workflow associated with patients that that are the responsibility of each of the multiple tenants supported by the MTNCS 150. A more detailed description of the server 155 functionality will be undertaken below with reference to FIG. 3.

Figure 3:
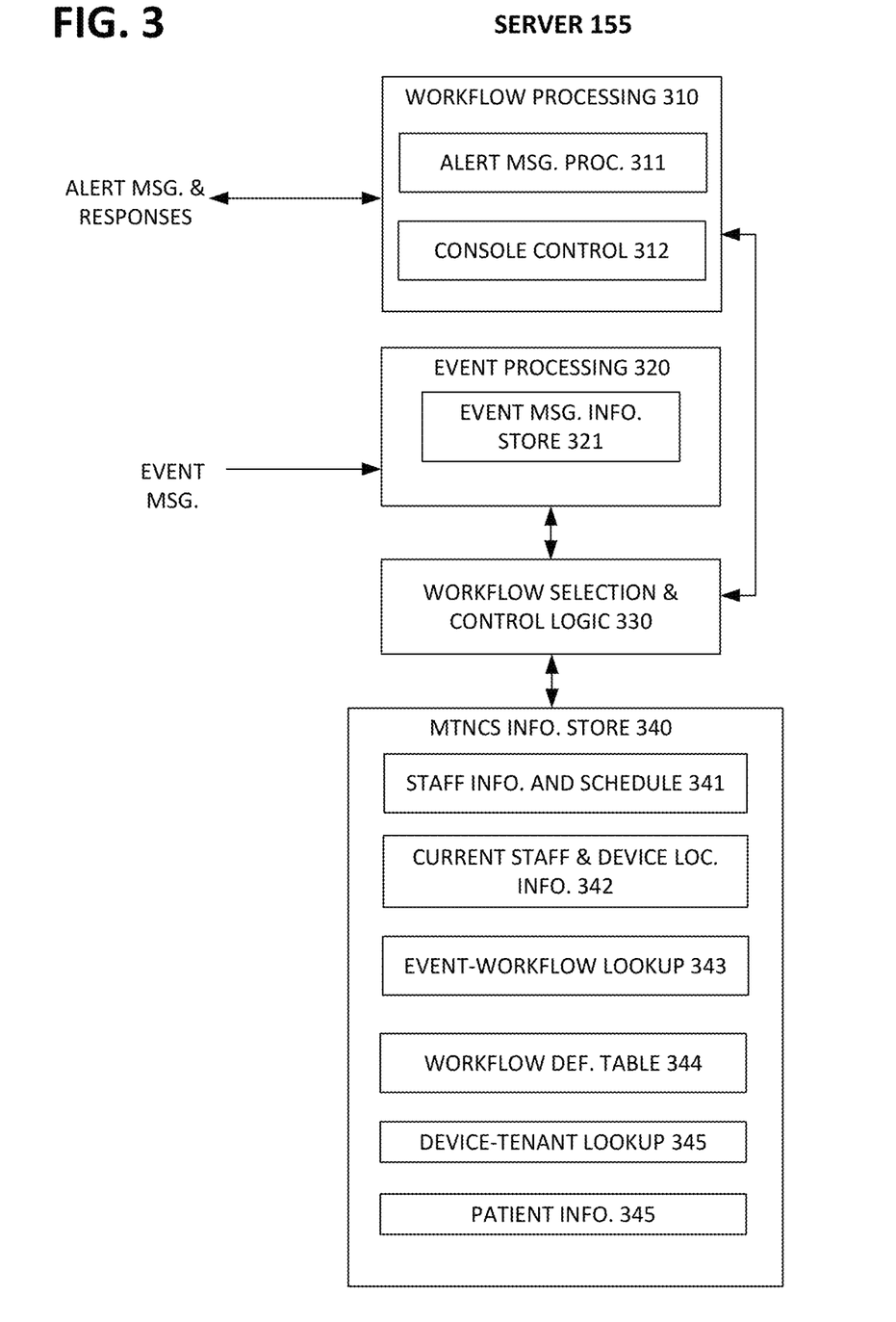
FIG. 3 is a diagram showing functional elements comprising a server 155.

FIG. 3 shows the server 155 comprising the MTNCS 150 having a workflow processing module 310, an event processing module 320, workflow selection and control logic 330, and a multi-tenant nurse call system (MTNCS) information store 340. Generally, the event processing module 320 receives event messages and maintains them in an event message information store 321 where the messages can be parsed so that the information in the message can be examined by the logic in order to select an appropriate workflow instance in the store 340. Once the appropriate workflow instance is selected, the logic 330 can control the workflow processing module 310 to generate alert messages having information directed to one or more staff, receive and process responses to the alert messages, and control the console to display or play certain information. While the store 340 is shown as being integral to the server 155, information in the store can be maintained in a separate database system and be accessible by the server as needed. Also, while the server 155 is shown in FIG. 3 to be running single instances of each of several different services (i.e., event message processing, alert message processing, workflow processing and location processing) each one or all of these services can be run on two or more virtual machines (not shown) each running on a separate physical server 155. A more detailed description of the server 155 functionality is included below.

Continuing to refer to FIG. 3, the event processing module 320 can receive and store event messages from patients (nurse call button), messages generated by smart patient beds having bed configuration information, messages from patient monitors having alert information of different priority levels or having physiological information (i.e., blood pressure, heart rate, respiratory rate, and other information), and messages generated by hospital staff to name only a few types of events. The event processor has functionality that operates to parse information in an event message and maintain the parsed information in a store that is accessible by the logic 330. The parsed information is comprised of among other things, an event type and the identity of a device that generated the event, timestamp information, patient ID, and any patient physiological information that may be included in the message. This parsed event information can be maintained, as previously described, in the store 321 at least until the workflow selection logic 330 is able to examine the information. The workflow selection logic 330 periodically examines the parsed event message information looking for, among other things, an event type, alert priority information, patient physiological information, and device ID. The logic 330 can use the event type ID to as a pointer into an event to workflow identity lookup table 343 (described later with reference to FIG. 4A) comprising the information store 340 to identify which one of a plurality of different workflow identities maintained in the store corresponds to that event type. The identity of a workflow can be used as a pointer into a workflow definition table 344 (described later with reference to FIG. 4B) that has a plurality of workflow definitions and associated tenant configuration information corresponding to each workflow. Further, the logic 330 can use the device ID as a pointer into a device to tenant lookup table 345 (described later with reference to FIG. 4C) to identify which tenant the device is currently assigned to, and if the identified tenant matches a tenant associated with the workflow identified in the workflow definition, then the logic can proceed to start the workflow.

Still further with continued reference to FIG. 3, a workflow can be configured to have a self-correcting function, such that it can be paused in order for the MTNCS 150 to determine whether the event that triggered the workflow is transitory in nature (i.e., does not occur again during some specified period of time). In this case, the workflow can be configured to have a suspend step, which allows the logic 330 to control the operation of a workflow to be temporarily paused at the time the suspend step is processed, or to stop a workflow in progress. More specifically, if a workflow is triggered to start when a particular type of event message is received (i.e., an event message having high-priority alert information generated by a patient monitor as the result of physiological information it detects), the logic 330 can operate to temporarily pause the processing of the workflow at a suspend step until the logic detects a specified number (selected, configurable threshold number) of subsequent event messages of the same type within some specified/configurable maximum period of time. This maximum period of time and the number of subsequent event messages of the same type can be specified by a system administrator and configured into the work flow suspend step. If during the time the processing of the workflow is suspended the logic does not detect a number of similar event messages that are equal to or greater than the threshold number value, then the processing of the workflow can be terminated without sending any notifications or any further notification to staff members. Alternatively, if after the workflow has been suspended the logic detects a number of subsequent separate instances of events, that are of the same type that triggered the workflow, that is greater than or equal to the specified threshold value (i.e., an integer value), then the logic can resume processing the workflow steps. An example of a workflow configured to have a suspend step will be described later with reference to FIG. 5B and the operation of the logic 330 to process a workflow having such a suspend-step will be described later with reference to FIGS. 6A and 6B. Continuing to refer to FIG. 3, and according to another embodiment, an auto-stop process, running in the background, can control a workflow to automatically stop (i.e., processing on the workflow terminated) at any time subsequent to the workflow being triggered to start and prior to a last step being processed if the logic 330 does not detect a particular number of subsequent, separate instances of an event message, similar to the one that triggered the workflow, that is equal to or greater than a threshold number. The threshold number can be selected by a systems administrator and employed to configure the workflow. An example of a workflow automatically stopping is illustrated with reference to FIG. 5C, and the operation of the logic 330 to process a workflow to automatically stop will be described later with reference to FIGS. 6A and 6B.

As described previously, the workflow definition table 344 is comprised of a plurality of workflow definitions and associated tenant configuration information, and each one of the workflow definitions has a set of two or more ordered business rules. According to one embodiment, if a workflow is determined to be associated with a tenant to whom the device is assigned, then the logic proceeds to start the workflow. A detailed description of the table 344 is provided later with reference to FIG. 4B. Once an appropriate workflow is identified, the logic 330 operates on the identified workflow to initiate a series of actions/steps (wherein the series of actions comprises a set of ordered business rules) that once completed result in the completion of the workflow. As described previously, any set of ordered business rules can be shared between two or more tenants and each rule is operated on by the logic 330 to initiate some action or activity to be performed by an individual or device currently assigned to one of the tenants or by the MTNCS or both. Also, as previously described, device configurations can be shared among two or more tenants. This sharing of a device configuration among tenants allows the device to be physically shared among tenants in a transparent manner and saves the time it would otherwise take to configure a device to operate when being utilized by any one of multiple tenants. A table having device and associated tenant configuration information is described later with reference to FIG. 4D.

Figure 4A:
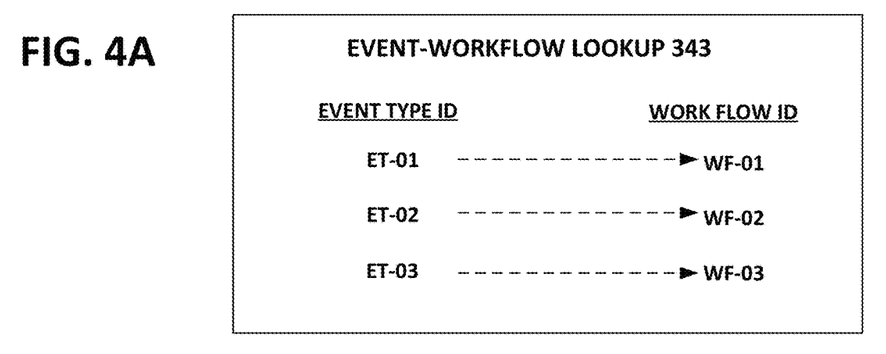
FIG. 4A is a diagram illustrating an event-workflow lookup table 343.
Figure 4B:
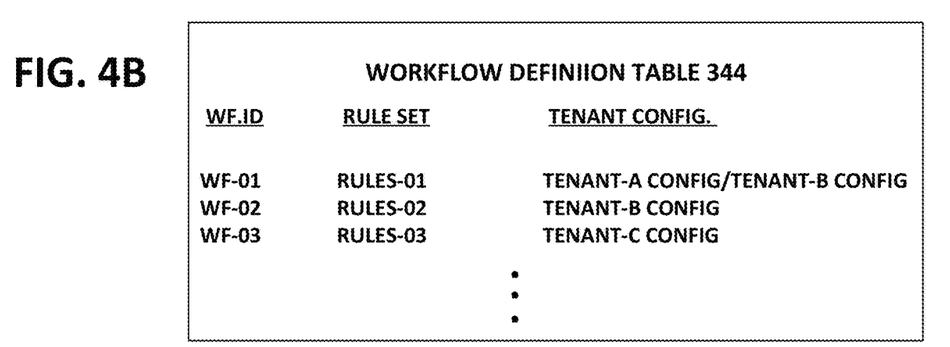
FIG. 4B is a diagram illustrating a workflow definition table 344.
Figure 4C:
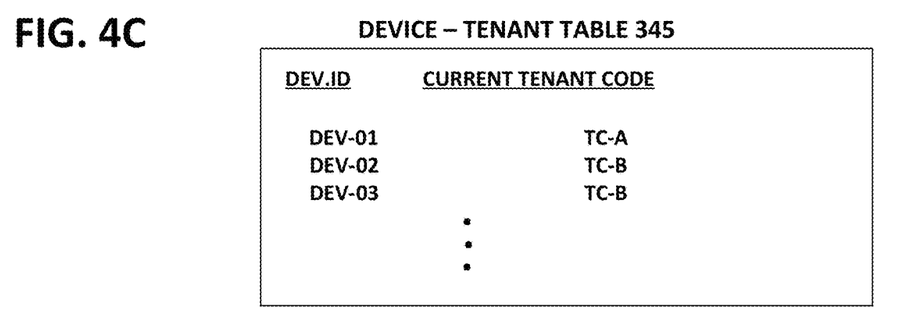
FIG. 4C is a diagram illustrating a device-tenant table 345.
Figure 4D:
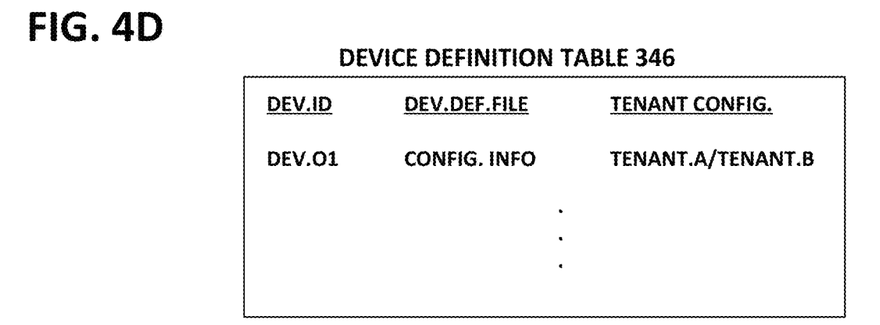
FIG. 4D is a diagram illustrating a device definition table 346.

FIG. 4A illustrates a format that information comprising a workflow lookup table 343 can take. The logic 330 uses an event type ID parsed from an event message to look up a corresponding workflow. The first column labeled "Event Type ID" is a list comprised of unique identities for each one of a plurality of different event types that can be generated by different devices operating in any one or in a multiple of tenant environments. The next column labeled "WF.ID" is a list comprised of a plurality of workflows, each one of which is shown to be associated with a particular event type. FIG. 4B illustrates a format for the workflow definition table 344 in which the column labeled "WF.ID" has a list of unique workflow identities that can be operated on by the logic 330. The second column labeled "Rule Sets" is a list comprised of sets of ordered business rules or workflow steps, with each set having two or more rules. An example set of ordered business rules will be described later with reference to FIG. 5. The third column in FIG. 4B is labeled "TENANT CONFIG." and each entry in this column is comprised of the identity of one or more tenants for which an associated workflow can be run. FIG. 4C illustrates a format for a device to tenant lookup table 345 that can be used by the logic 330 to determine which of a plurality of tenants each device is assigned to. A first column in the table 334 is labeled "Dev.ID", and it has a list of unique device identities that can be operating on by any one of a plurality of assigned tenant environments, and a second column labeled "Current Tenant Code" is comprised of a list of unique tenant codes (TC) assigned to the tenants comprising the hospital system 100. And finally, FIG. 4D illustrates a format for a device definition table 346 that has a list of device identities in a first column labeled "Dev.ID" that is comprised of a list of unique device identities, and the corresponding configuration files in a second column labeled "Dev.DEF.File", and a listing of related tenant configuration information in a third column labeled "Tenant.Config.".

Figure 4E:
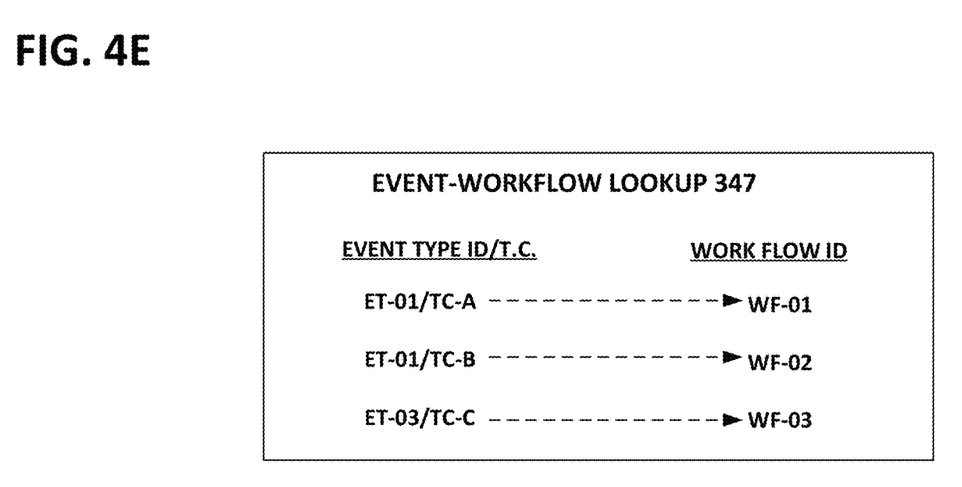
FIG. 4E is a diagram illustrating an event-workflow lookup table 347.

As described previously, any workflow comprised of a set of ordered business rules can be shared between two or more tenants, and each workflow is operated on by the logic 330 to initiate some action or activity to be performed by an individual or device currently assigned to one of the tenants or by the MTNCS or both. Alternatively, and according to one embodiment, the MTNCS can be configured such that separate instances of the same event type generated by two different tenants can result in the selection of two different workflows. Such a configuration is shown with reference FIG. 4E. For example, in the case that the MTNCS is configured to start a different workflow when two different tenants generate the same type of event, the logic 330 can operate to use a device ID in an event message to determine which tenant generated the event message, and then use the event type information and the tenant ID to look up and then start an appropriate workflow.

Figure 5A:
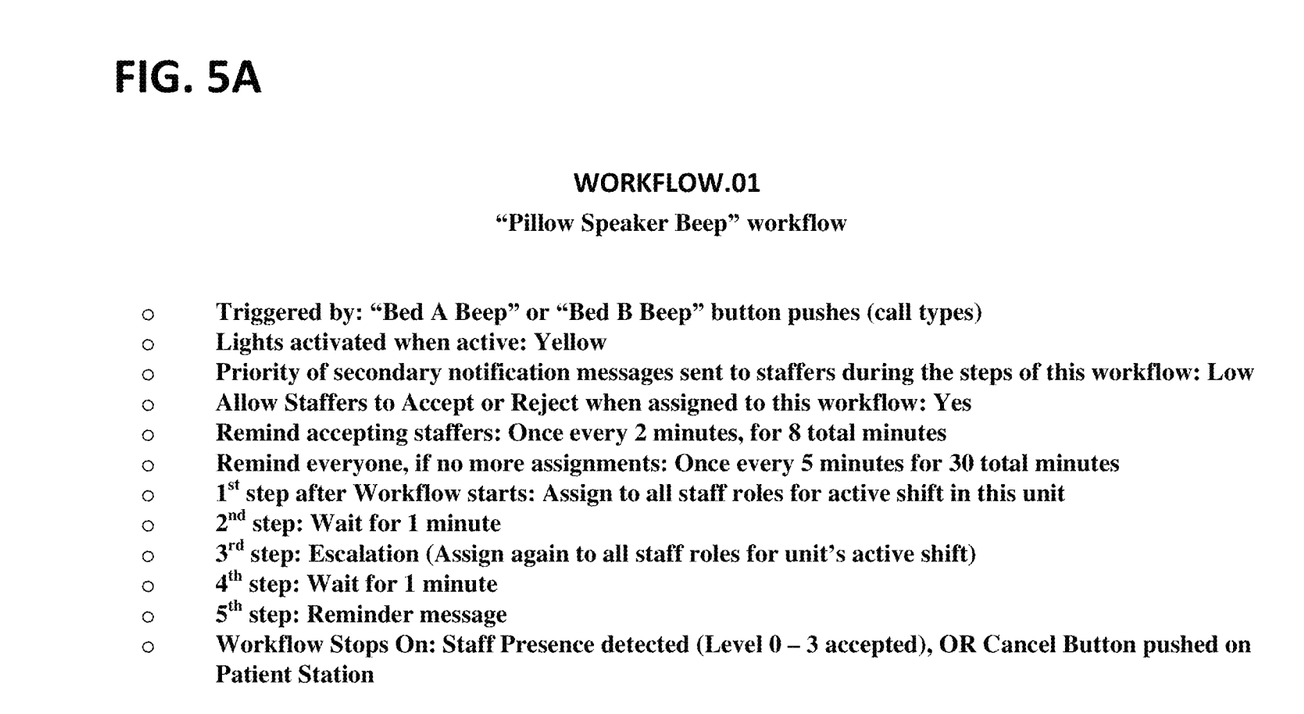
FIG. 5A is diagram illustrating rules comprising a workflow.

Next, we turn to a description of an exemplary workflow definition (WORKFLOW.01) maintained in the table 344 and shown with reference to FIG. 5A. The WORKFLOW.01 represents a set of ordered rules each one of which represents a step in an activity that is controlled by the MTNCS 150. The WORKFLOW.01 can be configured to be initialized by events generated by a nurse call button connected to a patient bed associated with one or more tenants, in this regard the workflow can be shared between tenants or not shared (workflow is partitioned). In this regard, the tenant configuration information entries in the workflow definition table 344 can be set to control whether a workflow is shared or partitioned among tenants. If for example, two tenants (tenant 1 and tenant 2 shown in FIG. 1) can be associated with WORKFLOW.01 (i.e., the tenant configuration entry for this workflow can be only one tenant "Tenant.A", or two tenants "Tenant.A/Tenant.B"), then WORKFLOW.01 can be started by the MTNCS 150 when it receives an event message from a nurse call device associated with either of these two tenants. This particular workflow (WORKFLOW.01) can be triggered by a patient depressing a nurse call button that is connected to their bed, for example. More specifically, the act of depressing the nurse call button generates an event message that includes, among other things, the event type and the device ID, bed number, etc. When operated on by the control logic 330, the first WORKFLOW.01 rule labeled WFR.1 causes a light (yellow in this case, but the workflow can be set to illuminate other colors of lights, red, green, etc.) to be illuminated on the console 156, which indicates to someone monitoring the console that a particular patient needs assistance. The second workflow rule is set such that the priority of sending secondary notification messages to staff is low, but this setting could be high or medium priority for example. The remaining rules in the WORKFLOW.01 are operated on by the logic 330 in sequence until the workflow is complete.

Figure 5B:
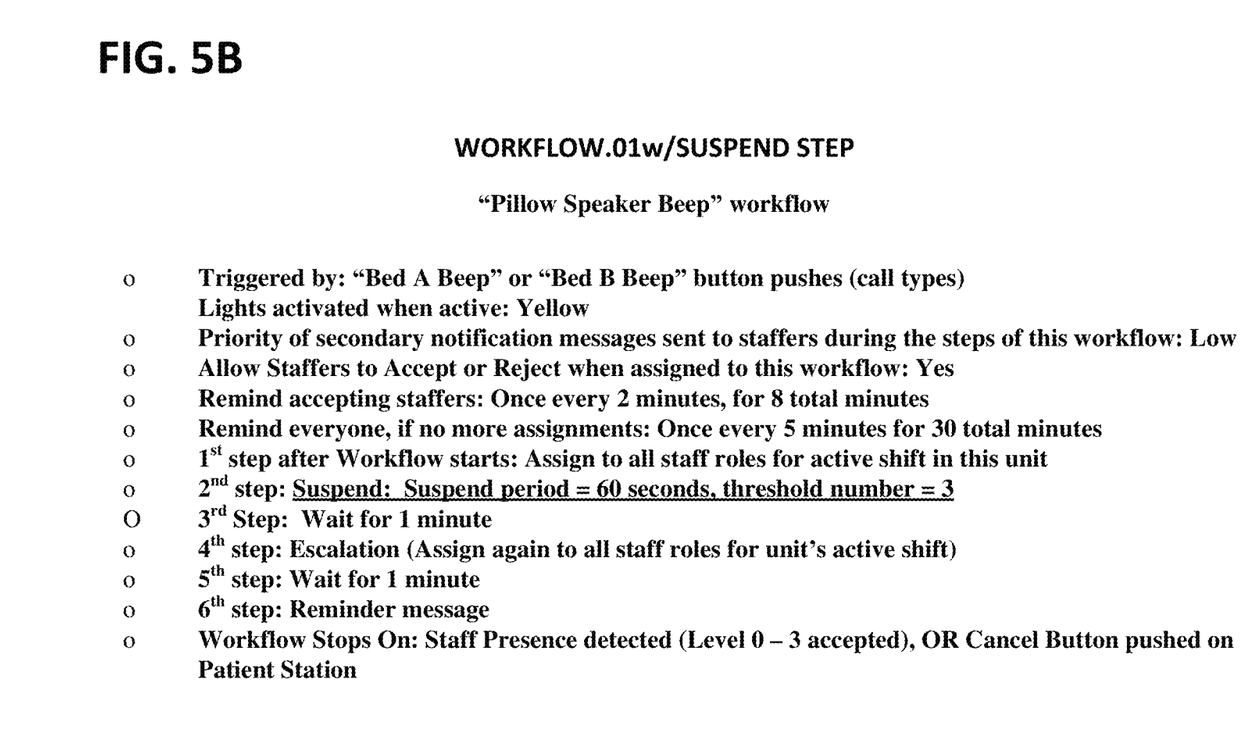
FIG. 5B is a diagram illustrating a workflow having a suspend step.

Alternatively with reference to FIG. 5B, after being triggered by a particular type of event, a workflow can be configured to pause at a particular step, waiting for a specified/threshold number of subsequent instances of the same type of event to be detected during some selected period of time. In this case, the workflow is configured to pause immediately after being triggered and to wait for sixty seconds for three subsequent events of the same type before proceeding to the next step. In the event that the threshold number of additional events are not detected, then the workflow can be terminated. While FIG. 5B shows the workflow being configured to have the suspend step processed immediately after the workflow is triggered, this does not necessarily have to be the case, as the workflow can be configured to have multiple suspend steps placed before or after any particular step in the workflow.

Figure 5C:
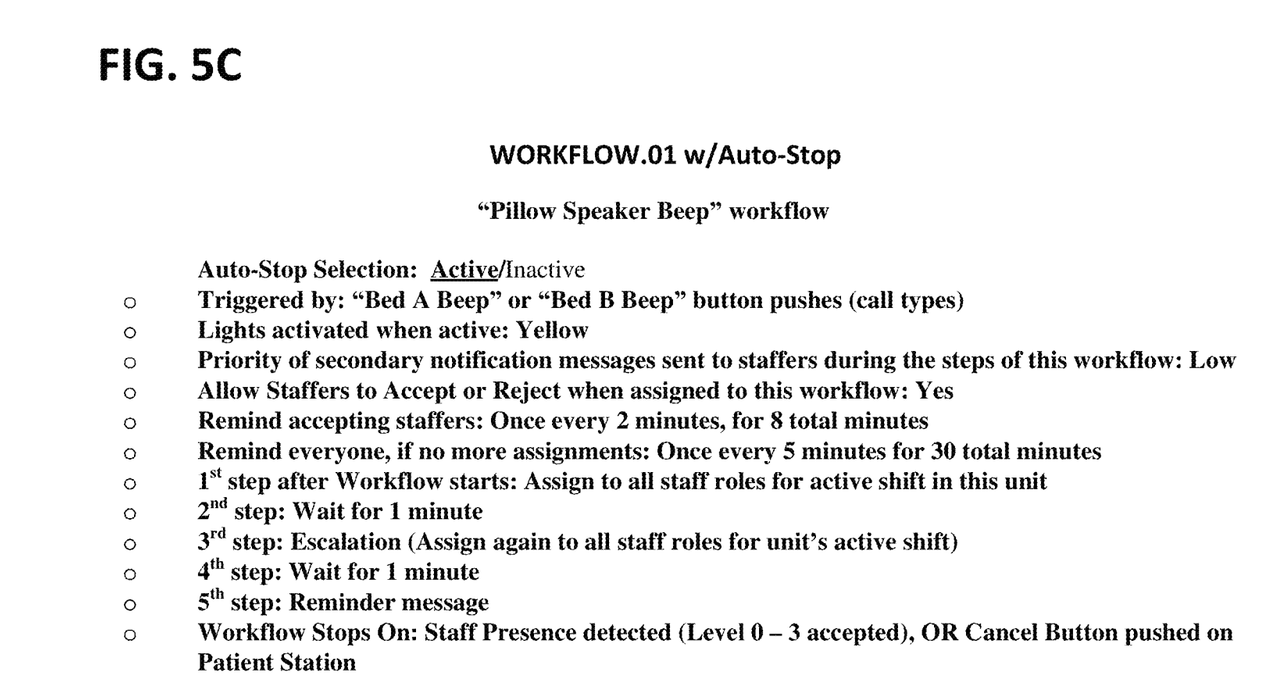
FIG. 5C is a diagram illustrating a workflow with auto-stop.

Alternatively with reference to FIG. 5C, if an Auto-Stop function is enabled, a workflow can be controlled to immediately stop after being triggered by a particular type of event. In this case, the workflow can be terminated at any point during the step-wise operation of a workflow if a threshold number of the same type of events that triggered the workflow are not detected during some specified period of time.

Sharing a workflow between tenants as described with reference to FIG. 3, can be advantageous in the event of a scheduled or unscheduled staff assignment change from one tenant to another tenant, or in the event that a medical device is moved from one tenant to another. Under these conditions, and according to an embodiment, the relevant MTNCS 150 tables do not need to be manually reconfigured every time a staff assignment or device assignment changes. Accordingly, some of the current tenant configuration information maintained in the workflow definition table 344 in association with one or more workflow definitions can be conditioned on a schedule associated with a staff member or on the location of a device. and which can be maintained in a staff information and schedule store 341 comprising the MTNCS information store 340. In this case, the control logic 330 can periodically examine the staff schedule information 341 maintained by the store 340 comprising the server 155, and if it detects that a staff member is scheduled to be assigned to Tenant.A on Monday and Tenant.B on Tuesday (due to a patient they are caring for being moved), then the MTNCS workflow definition table 344 in FIG. 4B can be configured such that the tenant configuration information that allows the workflow to operate in the Tenant.A environment can also operate in the Tenant.B environment for as long as the schedule has the staff member assigned to duty with Tenant.B.

Further, and according to another embodiment, this conditional workflow sharing between tenants can also be based upon a current location of the staff member, as determined by information generated by a location detection system such as RFID or beacon-based tracking system, or a GPS tracking system or other wireless location detection system and which is maintained in the information store 342 comprising the MTNCS information store 340. So, for example, if the schedule of a staff member assigns them to Tenant.A during a first period of time, and if during this time they are called away to care for a patient located at Tenant.B, then the system 150 can track the movement of the staff member to Tenant.B and provided the table 344 is configured to allow a workflow to be shared between with Tenant.B.

According to another embodiment, medical devices such as patient monitors, patient beds, nurse call devices, etc. can be configured such that events they generate can be processed by the MTNCS 150 when the device is operating in association with any one of a plurality of tenants. FIG. 4D illustrates a device definition table 346 in which device configuration information can be maintain with corresponding tenant configuration information. The tenant configuration information can be static or it can be modified dynamically depending upon the current location of the medical device. For example, if the device is only used by one particular tenant, then it can be configured such that the MTNCS 150 only processes event information from the device when it is operating in association with that one particular tenant. On the other hand, the current device location can be used to dynamically modify the tenant configuration information.

As previously described with reference to FIG. 3, the server 155 can support the operation of multiple virtual machines, each one of which can run one or more services supported by the MTNCS 150, such as the event message processing, alert message processing, workflow processing and location processing services. The services running on each VM can be assigned to support the operation of only one tenant or support the operation of multiple tenants. For example, if Tenant A has a large, busy facility with a number of emergencies, and Tenant B has a relatively low call volume, the MTNCS can be configured to host five instances each of the Messaging, NurseCall, Rules, and Tracking services. Each of these twenty total instances could be assigned to Tenant A, and only two instances of those same services could be assigned for Tenant B. In this way, the MTNCS 150 is more flexible than a traditional nurse call system, which would necessarily process events for all facilities in the organization. In part due to multi-tenant architecture, it is possible to tune CPU resources to be used according to loads associated with each of multiple tenants, therefor maintaining high performance while not incurring unnecessary expense for extra hardware or extra cloud VMs that are being underutilized. The event processing module 320 can be designed to track the call volume (or some other work load metric) of each tenant, and a virtual machine operating system or hypervisor (not shown and operating in conjunction with the workflow processing module 310 for example) can be controlled by the module 320 or the logic 330 to create and run more or fewer instances of virtual machines (each running some number of services) in association with particular tenants as determined by the work load associated with each tenant.

As described previously, the logic 330 operates to periodically examine information parsed from event messages and other types of messages received by the event processing module 320, and then uses the parsed information to select an appropriate workflow that it runs in conjunction with the workflow processing module 310. Each particular workflow is configured to run in response to an event, or other types of messages, received from a tenant. Depending upon the MTNCS configuration, some workflows can be configured to be triggered to run in response to particular event messages received from one particular tenant, other workflows can be triggered to run in response to messages received from two or more particular tenants, and different workflows can be triggered by the same type of event message receive received from two different tenants. Generally, each workflow is assigned a static tenant configuration (i.e., a system administrator is responsible for assigning tenants to workflows) This information can be comprised of staff scheduling information, current staff location or movement information, or it can be comprised of device location or movement information. Regardless, the decision to allow the system 150 to maintain static or dynamic tenant or device configurations is up to the tenants or the parent organization managing the operation of a MTNCS.

Figure 6A:
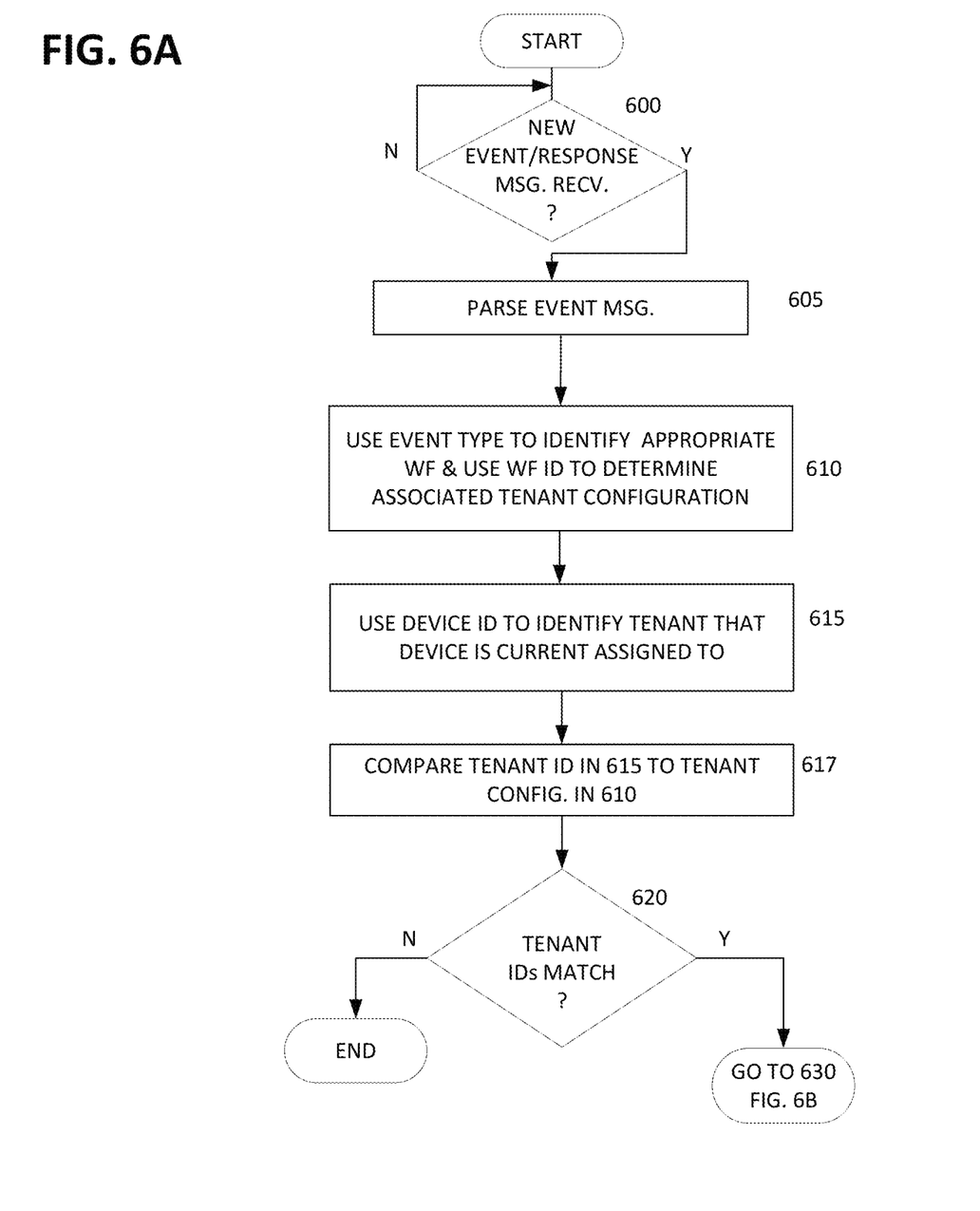
FIGS. 6A and 6B show a flow diagram illustrating a MTNCS 150 process.

FIG. 6A is a logical flow diagram illustrating how the MTNCS 150 can process event messages, or other incoming information in messages, to select and run an appropriate workflow. According to the embodiment illustrated in FIG. 6A, the logic 330 can operate on a workflow configured to run without interruption as described with reference to FIG. 5A, to operate on a workflow configured with one or more suspend steps, or to operate on a workflow configured with the auto-stop functionality. Further, according to the embodiment illustrated in FIG. 6A, the tenant assignment to workflows is statically maintained.

Subsequent to the MTNCS 150 being initialized, at 600 the system event processing module 320 can periodically receive a message (event message or other type of message) from a device (i.e., patient monitor) that is in communication with the system 150. After receiving the message, at 605 the event processing module 320 can parse information in the message looking for, among other things, event type information, patient physiological information, and the identity of a device that generated the message. The logic 330, at 610, periodically examines the information parsed at 605 and maintained by the module 320 looking for event type information, and uses the event type information as a pointer into the table 343 to identify a workflow that relates to the event type. Then at 615, the logic 330 uses the device identity as a pointer into the table 345 to determine the particular tenant to which the device is currently assigned, and at 617 the logic uses the identity of the workflow determined in 610 as a pointer into the table 344 to identify the tenant or tenants that are assigned to the identified workflow and compares these tenant identities to the identity of the tenant determined in 615, and if at 620 the logic detects a match the process proceeds to 630 in FIG. 6B, otherwise the process can be terminated.

Figure 6B:
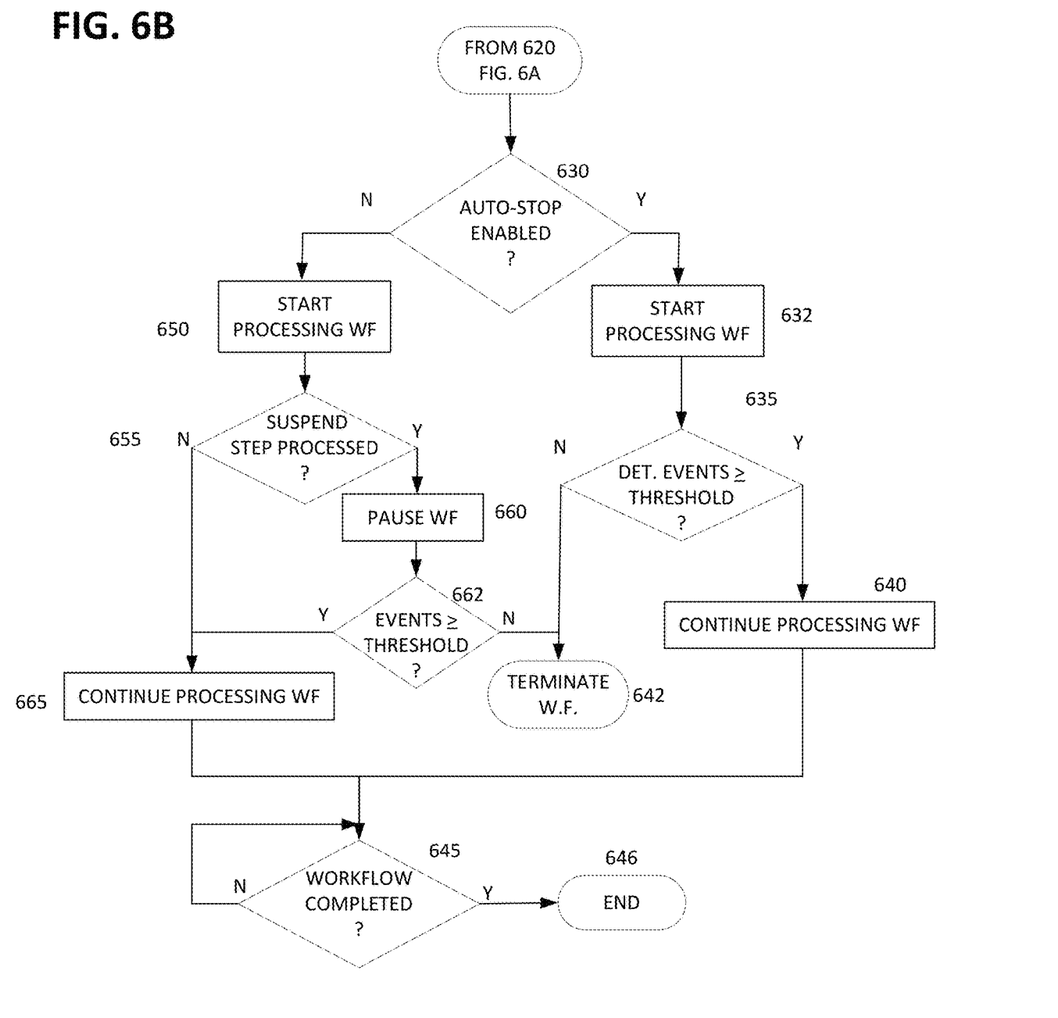

Referring now to 630 in FIG. 6B, the logic 330 operates to examine the workflow (WF) identified in 610 to determine whether or not it is configured with the auto-stop functionality enabled, and if so, the process proceeds to 632 and the logic 330 starts operating to process the steps comprising the selected workflow. On the other hand, if the auto-stop function is not enabled the process proceeds to 650. For a selected, configurable period of time (this period of time can be arrived at empirically or be based upon clinical experience) during which the workflow is running at 632, the logic 330 monitors the event processing functionality 320 looking for subsequent events of the type that triggered the current workflow to start, If the logic detects a number of subsequent, similar events to the one that triggered the workflow to be greater or equal to a threshold number during the configured period of time, then the workflow continues to be processed at 640 by the logic until at 645 the logic determines that all of the workflow steps have been processed, and the workflow is terminated at 646.

Continuing to refer to FIG. 6B, if at 630 to logic determines that the auto-stop functionality is not enabled, then the process proceeds to 650 and the workflow is triggered to start. If at subsequent to the workflow being triggered to start, and during the time the workflow is running, a suspend step is detected by the logic 330 at 655, then at 660 the progress of the workflow is paused for a selected, configurable period of time, which period of time can be selected base on empirical information or clinical experience. Otherwise at 665 the workflow is processed normally without pausing until the logic determines at 645 that the workflow has completed. Referring back to 660, during the time that the workflow is paused the logic at 662 monitors the event processing functionality 320 looking for subsequent events, of the type that triggered the current workflow to start. If at 662 the logic detects a number of subsequent, similar events to the one that triggered the workflow to be greater or equal to a threshold number during the configured period of time, then the workflow continues to be processed at 665 by the logic until all of the workflow steps have been processed, and the workflow is terminated at 646, otherwise the process proceeds to 642 and the workflow is terminated.

The forgoing description, for purposes of explanation, uses specific nomenclature to provide a thorough understanding of the invention. However, it will be apparent to one skilled in the art that specific details are not required in order to practice the invention. Thus, the forgoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

What is claimed is:

1. A method of processing an event message by a multi-clinical entity group nurse call system, comprising:
   a) configuring, via an event processor, the multi-clinical entity group nurse call system to select and process a workflow based upon a type of event message received and based upon an identity of a clinical entity group that generated the event message by:
      i) assigning, by an individual, a unique identity to each one of a plurality of clinical entity groups, wherein each one of the plurality of the clinical entity groups consists of one or more hospital specialty units, signaling devices, and messaging devices;
      ii) assigning a physical location to one or more of the plurality of clinical entity groups;
      iii) assigning an identity to each one of a plurality of medical devices comprising patient monitoring devices and associating each of the medical devices with different ones of the plurality of clinical entity groups; and
      iv) assigning a unique identity to each one of a plurality of workflows, wherein each instance of the plurality of the workflows is comprised of one or more ordered steps stored in a database system associated with the multi-clinical entity group nurse call system, and each one of the plurality of the workflows is selected for processing by the multi-clinical entity group nurse call system based upon an event message type generated by any one of the medical devices assigned to one of the plurality of clinical entity groups, and based upon an identity of the clinical entity group to which the medical device is assigned;
   b) receiving at the multi-clinical entity group nurse call system, via a communication network, a first event message from one of the medical devices;
   c) parsing, via the event processor, the first event message for an event message type and medical device identity information, and determining, via a logic, that the first event message is of a first type and was generated by a medical device associated with a first one of the plurality of the clinical entity groups;
   d) receiving at the multi-clinical entity group nurse call system a second event message;
   e) parsing, via the event processor, the second event message for an event message type and medical device identity information, and automatically determining, via the logic, that the second event message is of the first type and was generated by a medical device associated with a second one of the plurality of the clinical entity groups;
   f) selecting a first workflow to be processed for the first clinical entity group, and selecting a second workflow that is different than the first workflow to be processed for the second clinical entity group, each workflow being selected based upon both the event message type and an identity of the clinical entity group that generated the event message, and at least one of the selected workflows having a suspend step, wherein one or more of the first workflow and second workflow result in one or more of activating a visual or audio alert at a console and transmitting a message to the one or more messaging devices associated with a staff member associated with one or more of the workflow's clinical entity groups;
   g) starting and running, by the multi-clinical entity group nurse call system, the first and the second workflows until the system determines that a next step to be processed in the at least one of the workflows is a suspend step, immediately pausing the processing of the at least one workflow at the suspend step until at least one additional instance of the first type of event message is received, then immediately continuing to process the at least one of the workflows having the suspend step subsequent to receiving the at least one additional event message of the first type;

h) assigning the first workflow for the first clinical entity group to a first staff member tracked by a first wireless location tracking device when the first staff member is within a predetermined proximity to the physical location of a bed associated with the medical device that generated the first event message, where the bed and the medical device are each members of the first clinical entity group; and i) terminating at least one of the workflows during the suspend step if another one or more instances of the event message of the first type are not received prior to a selected, maximum period of time elapsing.

2. The method of claim 1, wherein the at least one of the workflows is configured to pause at the suspend step for up to a selected, maximum period of time.

3. The method of claim 1, further comprising the at least one of the workflows having two or more suspend steps, and a selected number of subsequent events of the first type can be the same for each suspend step, or can be different for some or all of the suspend steps.

4. The method of claim 3, wherein the one or more hospital specialty units are related by either one or both of a geographic position and the type of care provided.

5. The method of claim 1, wherein the first type of event message comprises information associated with a patient, a patient bed or an individual staff member assigned to the first or the second clinical entity group.

6. The method of claim 5, wherein the information associated with the patient comprises nurse call button information, patient bed status information, physiological information associated with the patient, or patient location information.

7. The method of claim 1, wherein each clinical entity group associated with the one or more specialty units in a healthcare facility is located in a contiguous area or non-contiguous areas in the healthcare facility, or is dispersed across multiple facilities in different geographic locations.

8. The method of claim 1, further comprising the at least first one of the plurality of workflows is configured to be shared with any two or more of the plurality of the clinical entity groups based upon the workflow configuration and a current assignment of a staff member to one of the clinical entity groups or based upon a current location of a staff member that coincides with one of the clinical entity groups.

9. A method of processing an event message by a multi-clinical entity group nurse call system, comprising:

a) configuring the multi-clinical entity group nurse call system to select and process a workflow based upon a type of event message received and based upon an identity of a clinical entity group that generated the event message by:

i) assigning, by an individual, a unique identity to each one of a plurality of clinical entity groups, wherein each one of the plurality of the clinical entity groups consists of one or more hospital specialty units, signaling devices, and messaging devices;

ii) assigning an identity to each one of a plurality of medical devices comprising patient monitoring devices and associating each of the medical devices with different ones of the plurality of clinical entity groups; and iii) assigning a unique identity to each one of a plurality of workflows, wherein each instance of the plurality of the workflows is comprised of one or more ordered steps stored in a database system associated with the multi-clinical entity group nurse call system, and each one of the plurality of the workflows is selected for processing by the multi-clinical entity group nurse call system based upon an event message type, generated by any one of the medical devices assigned to one of the plurality of clinical entity groups, and based upon an identity of the tenant to which the medical device is assigned;

b) receiving at the multi-clinical entity group nurse call system, via a communication network, a first event message;

c) parsing, via an event processor, the first event message for an event message type and medical device identity information, and determining, via a logic, that the first event message is of a first type and was generated by a first one of the plurality of the clinical entity groups, and receiving at the multi-clinical entity group nurse call system a second event message;

d) parsing, via the event processor, the second event message for an event message type and medical device identity information, and determining, via the logic, that the second event message is of the first type and was generated by a second one of the plurality of the clinical entity groups;

e) selecting a first workflow to be processed for the first clinical entity group and selecting a second workflow, that is different from the first workflow, to be processed for the second clinical entity group, each workflow being selected based upon both the event message type and an identity of the clinical entity group that generated the event message, wherein one or more of the first workflow and second workflow result in one or more of activating a visual or audio alert at a console and transmitting a message to the one or more messaging devices associated with a staff member associated with one or more of the workflow's clinical entity groups;

f) starting and running, by the multi-clinical entity group nurse call system, the first and the second workflows until it determines that a selected number of subsequent event messages of a same type as the first and second event messages are not received from one or the other of the first or second clinical entity groups, and immediately terminating the workflow being processed for the clinical entity group from which subsequent event messages of the first type are not received;

g) assigning a physical location to one or more of the plurality of clinical entity groups and assigning the first workflow for the first clinical entity group to a first staff member tracked by a first wireless location tracking device when the first staff member is within a predetermined proximity to the physical location of a bed associated with the medical device that generated the first event message, where the bed and the medical device are each members of the first clinical entity group; and h) terminating at least one of the workflows during a suspend step if another one or more instances of the event message of the first type are not received prior to a selected, maximum period of time elapsing, wherein the plurality of medical devices comprises a vital statistic monitoring device and a non-vital statistic monitoring device, and the vital statistic monitoring device generates an event message having a high-priority characteristic.

10. The method of claim 9, wherein a background process running on the multi-clinical entity group nurse call system tracks the number of subsequent event messages of the first type that are received after the first and the second workflows are started.

11. The method of claim 9, wherein the first type of event message comprises information associated with a patient, a patient bed or an individual staff member assigned to the first or the second clinical entity group.

12. The method of claim 11, wherein the information associated with the patient comprises nurse call button information, patient bed status information, physiological information associated with the patient, or patient location information.

13. The method of claim 9, wherein the one or more hospital specialty units comprising the clinical entity group are related by either one or both of a geographic position and the type of care provided.

14. The method of claim 9, wherein each clinical entity group associated with the one or more specialty units in a healthcare facility is located in a contiguous area or non-contiguous areas in the healthcare facility, or is dispersed across multiple facilities in different geographic locations.

15. A system for processing machine readable event messages, comprising:
   a) a plurality of uniquely identified clinical entity groups in communication with a network, wherein each one of the plurality of the clinical entity groups consists of one or more hospital specialty units, signaling devices, and messaging devices;
   b) a multi-clinical entity group nurse call system connected to the network comprising: a computational device;
      i) a display device; and
      ii) a store of clinical entity group related information maintained in a database system associated with and accessible by the multi-clinical entity group nurse call system; wherein the multi-clinical entity group nurse call system receives, via a communication network, a first event message, parses, via an event processor, the first event message for an event message type, and determines, via a logic, that the first event message is of a first type and was generated by a medical device comprising patient monitoring devices and associated with a first one of the plurality of the clinical entity groups, and receives, at the multi-clinical entity group nurse call system, a second event message, parses, via the event processor, the second event message for an event message type, and determines, via a logic, that the second event message is of the first type and was generated by a medical device comprising patient monitoring devices and associated with a second one of the plurality of the clinical entity groups; and
   wherein the multi-clinical entity group nurse call system selects a first workflow to be processed for the first clinical entity groups, and selects a second workflow, that is different than the first workflow, to be processed for the second clinical entity groups, each workflow being selected based upon both the event message type and an identity of the clinical entity groups that generated the event message, and at least one of the selected workflows having a suspend-step;
   wherein the multi-clinical entity group nurse call system assigns a physical location to one or more of the plurality of clinical entity groups and the multi-clinical entity group nurse call system assigns the first workflow for the first clinical entity groups to a first staff member tracked by a first wireless location tracking device when the first staff member is within a predetermined proximity to the physical location of the first clinical entity groups; and
   wherein the multi-clinical entity group nurse call system starts and runs the first and the second workflows until it determines that, for at least one of the first and second workflows, a next step to be processed is a suspend step, immediately pauses the processing of the at least one workflow at the suspend step until at least one additional instance of the first type of event message is received, and immediately continues to process the at least one of the workflows having the suspend step subsequent to receiving the at least one additional event message of the first type, and terminates at least one of the workflows during the suspend step if another one or more instances of the event message of the first type are not received prior to a selected, maximum period of time elapsing, wherein one or more of the first workflow and second workflow result in one or more of activating a visual or audio alert at a console and transmitting a message to the one or more messaging devices associated with a staff member associated with one or more of the workflow's clinical entity groups.

16. The system of claim 15, wherein the at least one of the workflows is configured to pause at the suspend step for up to a selected, maximum period of time.

17. The system of claim 15, further comprising the at least one of the workflows having two or more suspend steps, and a selected number of subsequent events of the first type can be the same for each suspend step, or can be different for some or all of the suspend steps.

* * * * *